DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JULY 25, 1972

900. O.G. 1230

T900,014

SEPARATION OF N-ISOPROPYLACRYLAMIDE FROM SULFURIC ACID SOLUTIONS THEREOF

Hans K. Dietl, Rte. 8, Seneca Road 37664, and Alan E. Lewis, 814 Afton St. 37660, both of Kingsport, Tenn.

Filed Sept. 25, 1970, Ser. No. 75,423
Int. Cl. C07c *103/00*
U.S. Cl. 260—561 N
1 Sheet Drawing. 11 Pages Specification

N-isopropylacrylamide is produced by reaction between acrylonitrile and isopropyl alcohol in concentrated sulfuric acid. In order for the n-isopropylacrylamide to be used in various industrial processes it must be isolated from its sulfuric acid solution. This may be accomplished by (1) dilution of the solution with water, (2) extracting the n-isopropylacrylamide content of the dilute solution with an organic solvent for n-isopropylacrylamide such as methylene chloride or chloroform, and (3) evaporating off the solvent from the n-isopropylacrylamide-solvent solution, whereby pure n-isopropylacrylamide is obtained.

July 25, 1972 H. K. DIETL ET AL T900,014
SEPARATION OF N-ISOPROPYLACRYLAMIDE FROM SULFURIC ACID SOLUTIONS THEREOF
Filed Sept. 25, 1970
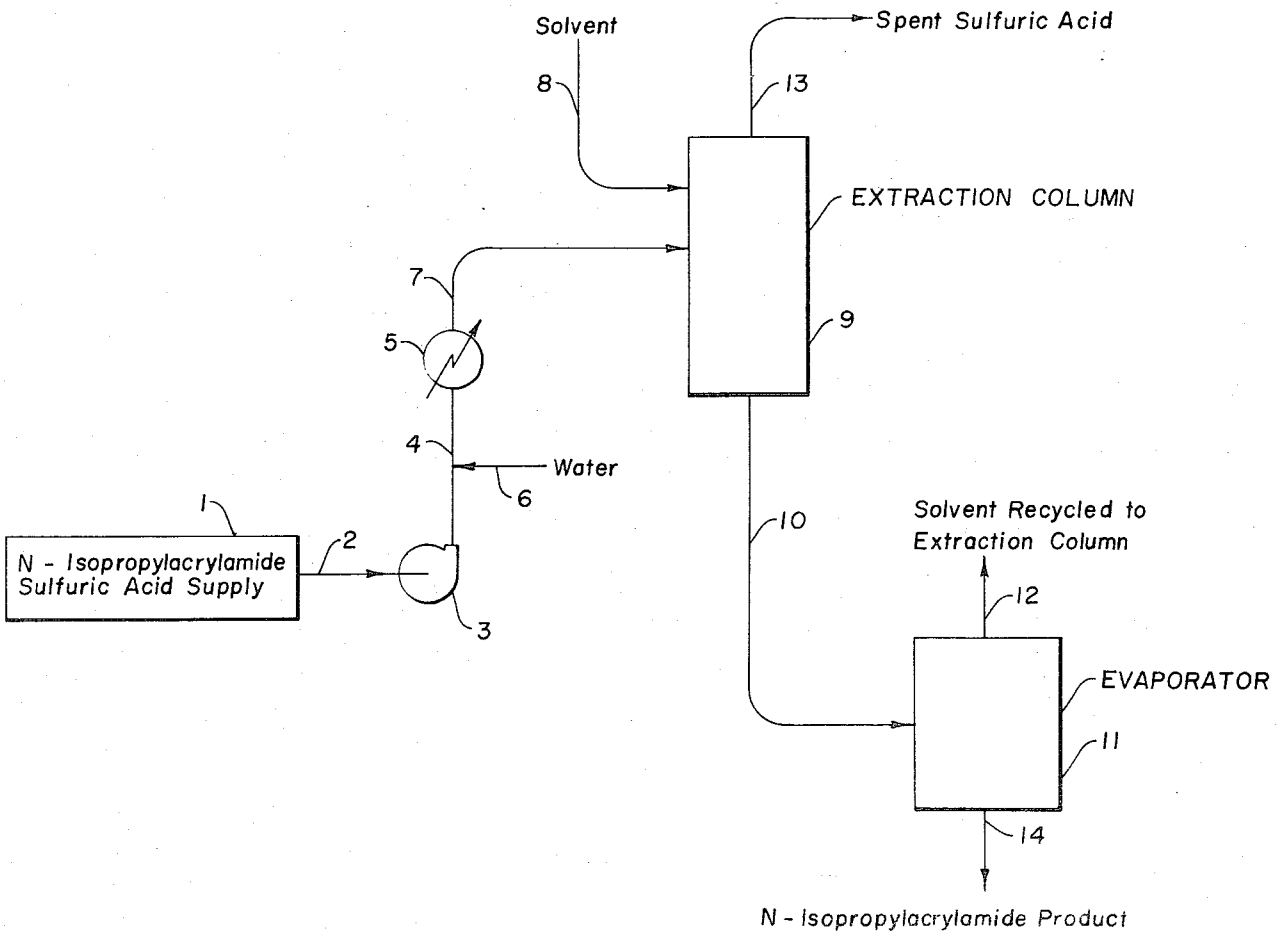
A. E. LEWIS
HANSK. DIETL
INVENTORS
BY Cecil D. Quillen Sr.
Daniel D. Reece Jr.
ATTORNEYS